(12) United States Patent
DiLorenzo

(10) Patent No.: US 9,072,594 B2
(45) Date of Patent: Jul. 7, 2015

(54) DYNAMIC TRACTION APPARATUS

(71) Applicant: John DiLorenzo, Bayville, NY (US)

(72) Inventor: John DiLorenzo, Bayville, NY (US)

(73) Assignee: John Dilorenzo, Bayville, NY (US)

( * ) Notice: Subject to any disclaimer, the term of this patent is extended or adjusted under 35 U.S.C. 154(b) by 172 days.

(21) Appl. No.: 13/710,774

(22) Filed: Dec. 11, 2012

(65) Prior Publication Data

US 2013/0178777 A1 Jul. 11, 2013

Related U.S. Application Data

(60) Provisional application No. 61/569,362, filed on Dec. 12, 2011.

(51) Int. Cl.
*A61F 5/00* (2006.01)
*A61F 5/048* (2006.01)

(52) U.S. Cl.
CPC ..................... *A61F 5/048* (2013.01)

(58) Field of Classification Search
CPC ........... A61F 5/048; A61G 2007/0509; A61G 2007/0514; A61G 2007/0516; A61G 2007/052; A61G 2007/0524; A61G 2007/0527; A61G 2203/20; A61G 2203/74; A61G 7/00; A61G 7/002; A61G 7/02; A61G 7/05; A61G 7/0506
USPC ................... 128/878–879; 602/20–28, 32–36
See application file for complete search history.

(56) References Cited

U.S. PATENT DOCUMENTS

| | | | | | |
|---|---|---|---|---|---|
| 4,602,620 | A | * | 7/1986 | Marx | 602/21 |
| 5,441,480 | A | * | 8/1995 | Kane et al. | 602/36 |
| 5,876,363 | A | * | 3/1999 | Marx | 602/21 |
| 6,093,162 | A | | 7/2000 | Fairleigh et al. | |
| 7,001,352 | B2 | | 2/2006 | Farrell et al. | |
| 7,833,183 | B2 | | 11/2010 | Padova | |
| 7,892,194 | B2 | | 2/2011 | Farrell et al. | |
| 8,328,744 | B2 | | 12/2012 | Farrell et al. | |

OTHER PUBLICATIONS

Werntz et al.: "A New Dynamic Splint for Postoperative Treatment of Flexor Tendon Injury", *The Journal of Hand Surgery*, 14A: pp. 559-566, 1989; (8 pages).
Becker et al.: "A Constant Tension Dynamic Splint". *Plastic and Reconstructive Surgery*, vol. 66:1, pp. 48-150, 1980; (3 pages).
Slattery et al.: "A Modified Kleinert Controlled Mobilization Splint Following Flexor Tendon Repair". *The Journal of Hand Surgery*, vol. 9-B:2, pp. 217-218, 1984; (2 pages).

(Continued)

*Primary Examiner* — Michael Brown
(74) *Attorney, Agent, or Firm* — Carter DeLuca Farrell & Schmidt LLP

(57) ABSTRACT

A dynamic traction apparatus is provided. A mounting portion includes a mounting portion that is configured to support a channel frame thereon. The channel frame includes one or more channels that extend along a length thereof and one or more corresponding resilient members positioned adjacent the channels. A bridge mount extends distally from the mounting portion and including a bridge extending transverse to a longitudinal axis defined through the mounting portion. The bridge includes one or more wheels disposed in substantial alignment with the channel(s) of the channel frame such that a coupling member extending through the channel(s) and coupled to the resilient member(s) is/are selectively coupleable to a finger of a patient.

9 Claims, 3 Drawing Sheets

(56) References Cited

OTHER PUBLICATIONS

Tonkin et al.: "Flexor Tendon Surgery-Today and Looking Ahead". *Clinics in Plastic Surgery*, vol. 13:4, pp. 221-242, 1986; (21 pages).

Rouzaud: "L'Assistant Dynamique Chiffré Par Ressort Spirale Étalonné Dans L'Orthèse De La Main". *Annales De Chirurgie De La Main*, vol. 6:3, 1987; (5 pages).

\* cited by examiner

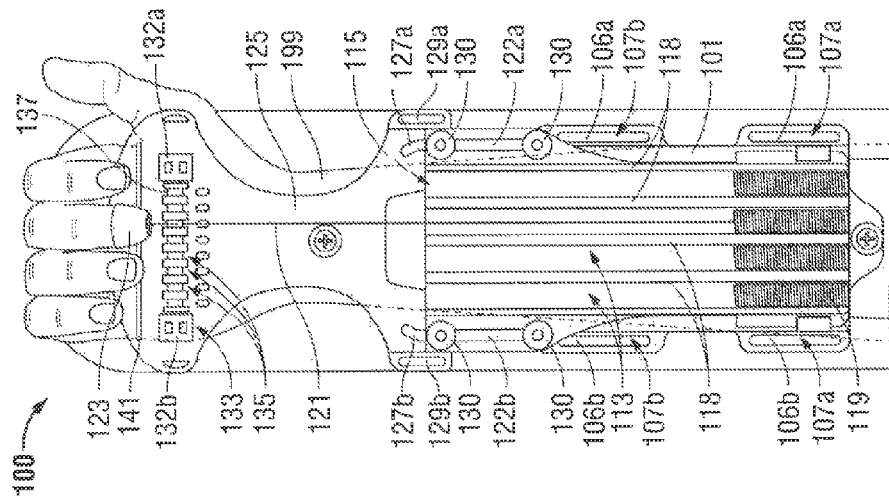
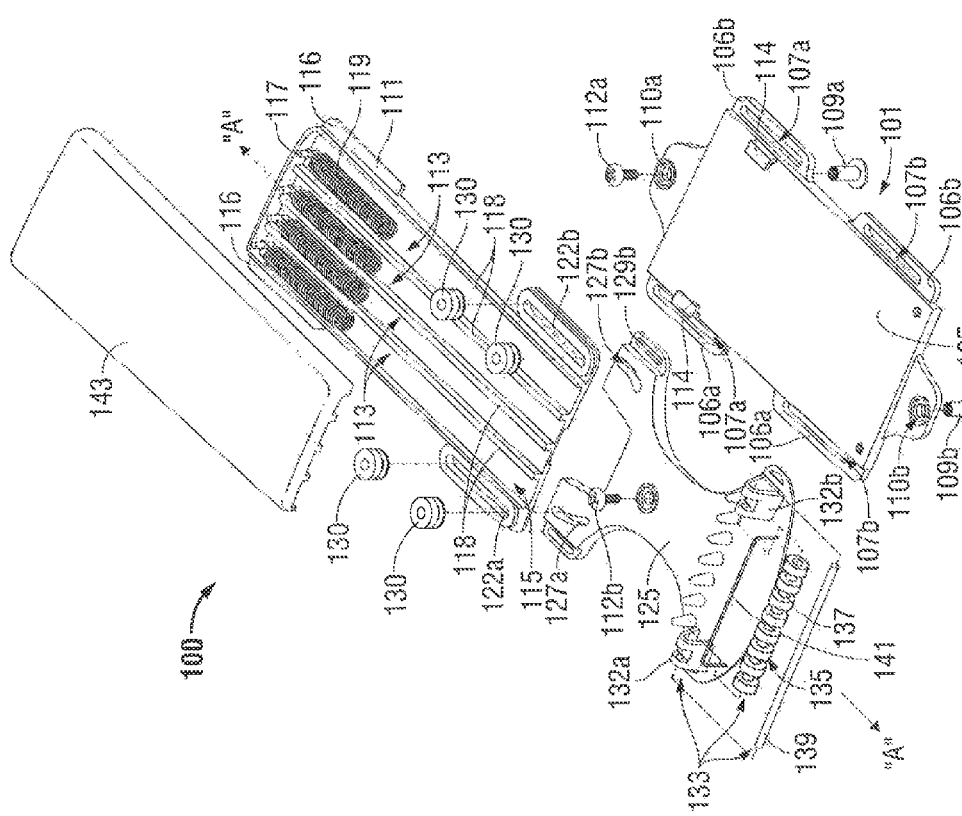

DYNAMIC TRACTION APPARATUS

CROSS-REFERENCE TO RELATED APPLICATIONS

This application claims the benefit of and priority to U.S. Provisional Application Ser. No. 61/569,362, filed by John DiLorenzo on Dec. 12, 2011, the entire contents of which is incorporated by reference herein.

BACKGROUND

1. Technical Field

The present disclosure relates to a dynamic traction apparatus and more particularly, to a dynamic traction apparatus configured for overall strengthening one or more components associated with a musculoskeletal system of a patient.

2. Background of Related Art

Management of tendon injuries may present a continuing challenge for therapists and patients to abide by specific protocols. Following tendon surgery, flexor and/or extensor repair, a surgeon may want to provide their patients with an effective protective splint with an appropriate traction. Early mobilization of a repaired tendon may reduce adhesions between tendons and a synovial sheath. Thus, early mobilization may be shown to increase tensile strength of the tendon following healing. Tendons of the mobilized digits also may show early and progressive strength gains.

Traction devices may include a predetermined selection of equipment, such as wires, posts, and hangers. Since the necessary equipment is predetermined before the formation of the traction device, many of the pieces of equipment may not be needed. In addition, the equipment may be exposed, such as the wires and posts, in a fashion which allows the user to become entangled with other items in which traction device may contact. Not only are such entanglements annoying, but may also expose the tendons that are attached to the device to damage.

SUMMARY in view of the foregoing, it may prove useful to provide a dynamic traction apparatus configured for overall strengthening of one or more components associated with a musculoskeletal system of a patient.

An aspect of the instant disclosure provides a dynamic traction apparatus. The dynamic traction apparatus includes a mounting portion that is configured to support a channel frame thereon. The channel frame includes one or more channels that extend along a length thereof and one or more corresponding resilient members positioned adjacent the channels. A bridge mount extends distally from the mounting portion and includes a bridge extending transverse to a longitudinal axis defined through the mounting portion. The bridge includes one or more wheels disposed in substantial alignment with the channel(s) of the channel frame such that a coupling member extending through the channel(s) and coupled to the resilient member(s) is/are selectively coupleable to a finger of a patient. The resilient members may be in the form of a coil spring. The coupling member may be a wire, a string, a cable or a cord.

The channel frame may include a plurality of channels and a corresponding plurality of resilient members that are positioned adjacent thereto. In this instance, a corresponding plurality coupling members may couple to a respective one of the resilient members and the bridge may include a plurality of wheels.

The mounting portion may include a pair of proximal strapping apertures and a pair of distal strapping apertures that are configured to receive corresponding straps therethrough that are configured to couple the dynamic traction apparatus to an arm of a patient.

The channel frame may include a pair of distal apertures that have a generally elongated configuration that are in alignment with a pair of corresponding proximal apertures on the bridge mount. The proximal apertures on the bridge mount may include a generally arcuate configuration and may be configured to allow pivotable movement of the bridge mount with respect to the channel frame.

The coupling devices may be configured for passage through the pair of distal apertures on the channel frame and proximal apertures on the bridge mount and may be configured to couple the channel frame and bridge mount one another. The coupling members may be configured to provide adjustment of the dynamic traction device with respect to an arm of a patient when the dynamic traction device is coupled thereto.

The bridge may include a pair of opposing upright extensions that are configured to support an axle thereon. The wheel(s) may be rotatably disposed on the axle A cover portion may be removably coupleable to the channel frame and configured to substantially enclose the channel frame when coupled thereto. The mounting portion, mounting portion, channel frame, cover and bridge mount are formed from a relatively rigid plastic material.

An aspect of the instant discloser provides a dynamic traction apparatus configured for removably coupling to an arm of a patient that is in traction. A mounting portion is configured to support a channel frame thereon. The channel frame includes one or more channels defined therein and that extend along a length thereof and at least one corresponding resilient member is positioned adjacent the channel(s). One or more resilient members are operably coupled to the frame. One or more coupling members include a proximal end coupled to the resilient member(s). A bridge mount is removably coupleable to the channel frame and includes a bridge extending transverse to a longitudinal axis defined through the mounting portion. The bridge includes one or more wheels that are disposed in substantial alignment with the channel(s) of the channel frame such that a distal end of the coupling member(s) is/are selectively coupleable to a finger of a patient.

The channel frame may include a plurality of channels and a corresponding plurality of resilient members that are positioned adjacent thereto. In this instance, a corresponding plurality coupling members may couple to a respective one of the resilient members and the bridge may include a plurality of wheels.

The mounting portion may include a pair of proximal strapping apertures and a pair of distal strapping apertures that are configured to receive corresponding straps therethrough that are configured to couple the dynamic traction apparatus to an arm of a patient.

The channel frame may include a pair of distal apertures that have a generally elongated configuration that are in alignment with a pair of corresponding proximal apertures on the bridge mount. The proximal apertures on the bridge mount may include a generally arcuate configuration and may be configured to allow pivotable movement of the bridge mount with respect to the channel frame.

The coupling device(s) may be configured for passage through the pair of distal apertures on the channel frame and proximal apertures on the bridge mount and may be configured to couple the channel frame and bridge mount one another. The coupling members may be configured to provide adjustment of the dynamic traction device with respect to an arm of a patient when the dynamic traction device is coupled thereto.

The bridge may include a pair of opposing upright extensions that are configured to support an axle thereon. The wheel(s) may be rotatably disposed on the axle.

A cover portion may be removably coupleable to the channel frame and configured to substantially enclose the channel frame when coupled thereto. The mounting portion, mounting portion, channel frame, cover and bridge mount are formed from a relatively rigid plastic material.

BRIEF DESCRIPTION OF THE DRAWINGS

Various embodiments of the presently disclosed apparatus are described herein with reference to the drawings, wherein:

FIG. 1D is an exploded view of the dynamic traction apparatus with parts separated;

FIG. 2 is a top, elevational view of dynamic traction apparatus shown in use;

DETAILED DESCRIPTION

Figure 1A:
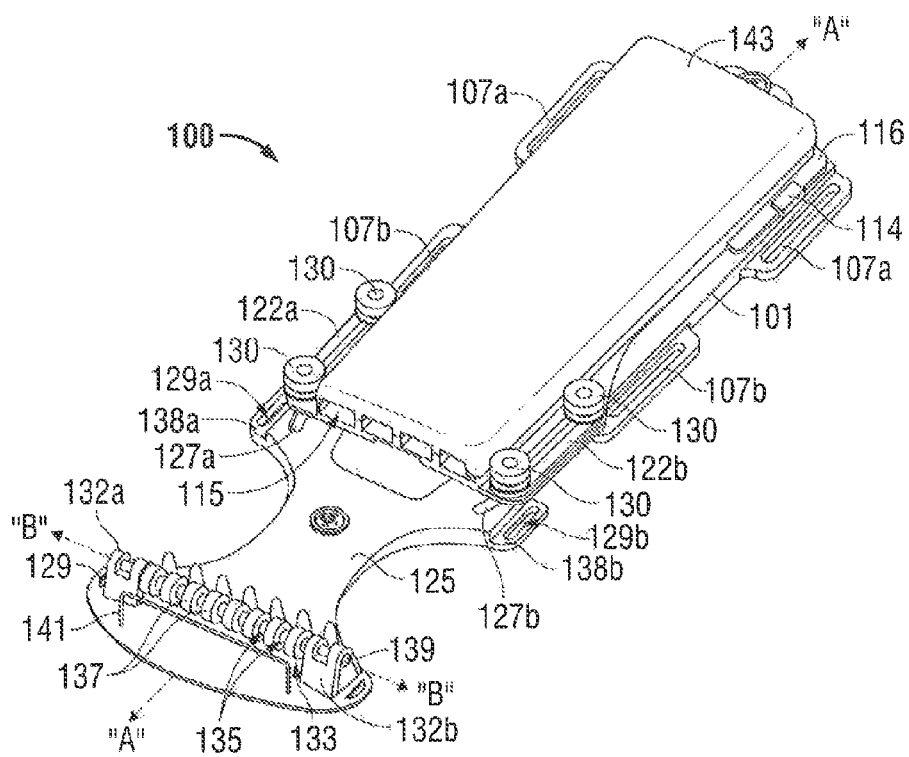
FIG. 1A is a perspective view of a dynamic traction apparatus according to an embodiment of the instant disclosure.

Embodiments of the presently disclosed apparatus are described in detail with reference to the drawing figures wherein like reference numerals identify similar or identical elements. As used herein, the term "distal" refers to the portion that is being described which is further from a user, while the term "proximal" refers to the portion that is being described which is closer to a user. Moreover, limb is defined herein as including legs and or arms of a patient.

In accordance with the instant disclosure, a dynamic traction apparatus is provided and is configured such that components associated therewith may be easily added to any brace and/or base device, e.g., a cast. As can be appreciated, this allows a professional, e.g. surgeon or therapist, the freedom to alter or create the device as dictated by a patient's changing needs. Moreover, the components of the dynamic traction apparatus may be partially encased by an optional cover and, thus, protected from incidental contact and/or entanglement with other objects, thereby reducing the likelihood of re-injury.

The dynamic traction apparatus described herein may be used as a brace for an injured limb, or attached to a brace for an injured limb for the purpose of strength training muscles, ligaments, tendons, bones, and anything else associate with the movement of digits (fingers, toes) of a patient. The dynamic traction apparatus may be easily attached to any splint, cast, or splint material, e.g., Exos splint. The dynamic traction apparatus may also incorporate a splint as part of the device to facilitate mounting on a limb.

As described herein, the dynamic traction apparatus may provide for full finger extension and specific limited passive exercises permitted at the PIP and DIP joints in an effort to impart about 3 mm to 5 mm of tendon excursion to the repaired tendon. The tension provided by, for example, one or more types of resilient members provide a reduced workload when compared to known devices. A bridge mount portion may be positioned near a Palmer crease and allows for a smooth glide with natural tendon actuation.

Referring to FIGS. 1A-2, a dynamic traction apparatus 100 (apparatus 100) is configured to couple to a volar or underside of limb 199 (e.g., an underside of a patient's wrist) and includes three (3) main components, a mounting portion 101, a channel frame 111 and a bridge mount portion 125. The aforementioned components may be formed from any suitable material, plastic, metal, etc. In the illustrated embodiment, mounting portion 101, channel frame 111 and bridge mount portion 125 are formed from a flexible, relatively rigid plastic.

Mounting portion 101 includes a generally elongated configuration having a patient contact side 103 (see FIG. 1C for example) and a mounting side 105 (FIG. 1D) configured to releasably couple to channel frame 111. Patient contact side 103 is configured to mount to a cast and/or a limb 199 of a patient (see FIG. 1C in combination with FIG. 2). One or more straps (not shown), such as Velcro® straps, may be utilized to attach mounting portion 101 and/or apparatus 100 to a patient in an embodiment, such as the illustrated embodiment, a pair of Velcro straps (not shown) are configured for receipt through corresponding proximal and distal strapping apertures 107a, 107b that are provided on respective lateral extensions 106a, 106b. Specifically, the apertures 107a, 107b are configured to allow one or more straps to pass therethrough for securing apparatus 100 to a cast that has been previously attached to an arm (or leg) of a patient. In some embodiments, screws, bolts, buttons, rivets, or any other suitable device and/or attachment method may be utilized in place of the straps to attach apparatus 100 to a limb of a patient.

A pair of lateral retaining clips 114 are provided at a proximal end of mounting portion 101 adjacent proximal strapping apertures 107a and are configured to slidably receive a pair of corresponding lateral flanges 116 that are disposed along a peripheral edge of channel frame 111 (FIG. 1A). Clips 114 and flanges 116 allow a user to couple channel frame 111 to mounting side 105 of mounting portion 101 (FIG. 1A). Alternatively, mounting portion 101 may be coupled to channel frame 111 via a mechanical interface, adhesive, or any other suitable coupling device, e.g., rivets, screws, snaps, buttons, zippers, pins, tape, Velcro®, and the like.

Optional proximal and distal support members 109a, 109b may be provided on coupling mounting portion 101 and may be configured to contact a cast, splint and/or limb when apparatus 100 is attached to a patient. Specifically, support members 109a, 109b allow a user to adjust or compensate for gaps that may be present between apparatus 100 and the cast and/or splint. To this end, support members 109a, 109b are received through corresponding proximal and distal apertures 110a, 110b are configured to couple to corresponding screws 112a, 112b. In use, screws 112a, 112b may be tightened and/or loosened via one or more suitable instruments, e.g., a screwdriver, accordingly to retract and/or extend support members 109a, 109b.

Continuing with reference to FIG. 1D, channel frame 111 includes a generally elongated configuration and defines a longitudinal axis "A-A," Channel frame 111 has one ore more Channels 113 defined therein. In the illustrated embodiments, for example, channel frame 111 defines four channels 113 that are configured for use with one or more fingers of a patient. In embodiments, five channels 113 may be utilized and may be configured for use with each finger of a patient. Channels 113 are defined by internal walls 118 and extend along a length of the channel frame 111. Channels 113 and internal walls 118 are configured to receive corresponding coupling members 121 and resilient members 119 therein (FIGS. 1D-2). Channels 113 are also configured to allow distal and proximal movement of resilient members 119 therealong when coupling members 121 are coupled to a finger of a patient.

Posts 117 are provided at a proximal end of channel frame 111 and are configured to couple to corresponding resilient members 119. In the illustrated embodiment, posts 117 include a generally circumferential configuration and extend upwardly from a top surface of channel frame 111 for coupling to proximal ends that of resilient members 119. Specifically, each of the proximal ends of resilient members 119 are provided with a corresponding eyelet or hook portion (not explicitly shown) that is configured to engage a corresponding post 117. Other types of devices may be utilized for coupling the proximal end of resilient members 119 to internal frame 111. For example, one or more protrusions, recesses, or the like may be utilized for coupling resilient members 119 to channel frame 111.

Resilient members 119 are configured to provide a resistive force to fingers of a patient when the fingers of a patient are coupled to apparatus 100. To this end, resilient member 119 may be any suitable type of spring (e.g., a linear spring, a rotational spring, coil spring, torsion spring, etc.), one or more biasing solid pieces of material, elastic band, magnet(s), or other suitable device component that is resistive to stretching/moving/bending/etc. In the illustrated embodiment, resilient members 119 are in the form of coil springs that are configured to provide a resistance that ranges from about 65 grams of force to about 100 grams of force when coupling members 121 are coupled to a finger of a patient and the finger is moved a predetermined distance distally. In an embodiment, resilient members 119 are configured to provide a resistance that ranges from about 0.1 grams of force to about 200 grants of force. In an embodiment, resilient members 119 are configured to provide a resistance that ranges from about 50 grams of force to about 150 grams of force. The proximal ends of resilient members 119 allow a surgeon or clinician to change-out resilient members 119 for resilient members having greater or less resistive forces. Resilient members 119 include a proximal end that is configured to couple to a corresponding post 117 and a distal end that is configured to couple to a proximal end of a coupling member 121.

Coupling members 121 are configured to selectively and removably couple to a corresponding finger of a patient (FIG. 2) for coupling the finger to a corresponding resilient member 119. Coupling members 121 may be any suitable coupling member including without limitation a wire, a string, a cable and/or a cord. In the illustrated embodiment, coupling members 121 are in the form of wires of suitable configuration. Coupling members 121 include a distal end that that is configured to couple to a finger of a patient through any suitable connection device and/or method. For example, finger caps, clips, adhesives, straps, tape, loops, ties, or other suitable device may be utilized to couple coupling members 121 to a finger of a patient. In the illustrated embodiment, for example, a finger cap 123 of suitable configuration is coupled to coupling member 121 via suitable coupling methods and is configured to releasably couple to a finger of a patient. In embodiments, finger cap 123 is removably coupled to a distal end of coupling member 121. Thus, in this embodiment, if a particular finger cap 123 does not properly fit on a finger of a patient, a finger cap 123 of different configuration or other coupling method (e.g., adhesive, loop and/or glue) may be utilized to couple coupling member 121 to a finger of a patient. In the instance where an adhesive is utilized, a distal end of coupling members 121 may be adhered to a center of a nail of a finger.

In embodiments, coupling members 121 may be configured in conjunction with resilient members 119 to form a portion of the resistance provided for a finger of a patient. In this particular embodiment, coupling members 121 may be elastic and, thus, provide a resistive force if pulled and stretched. In some embodiments, an elastic wire or string (not shown) may be mounted directly to the post 117 and/or other portion of the channel 113, thereby eliminating the need for a separate resilient member 119.

Figure 1B:
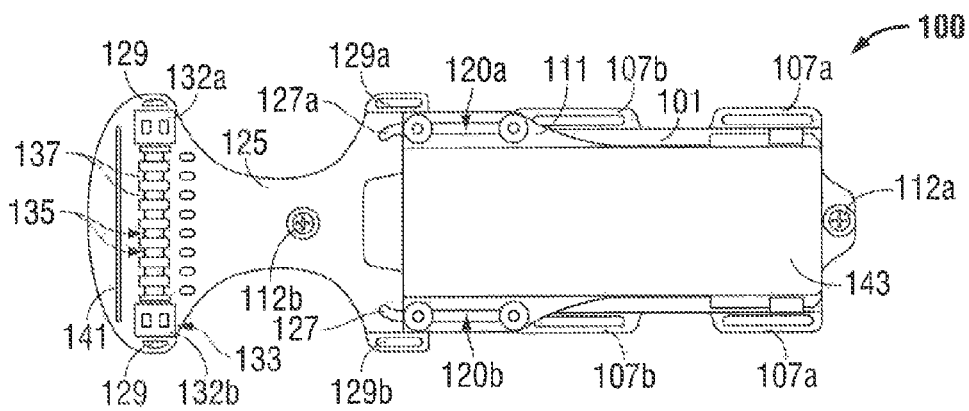
FIG. 1B is a top, elevational view of the dynamic traction apparatus depicted in FIG. 1A.
Figure 1C:
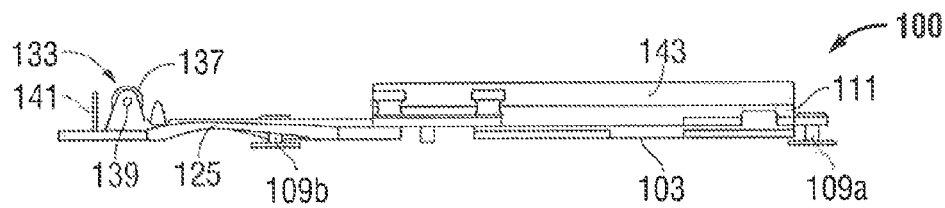
FIG. 1C is a side view of the dynamic traction apparatus.
Figure 3A:
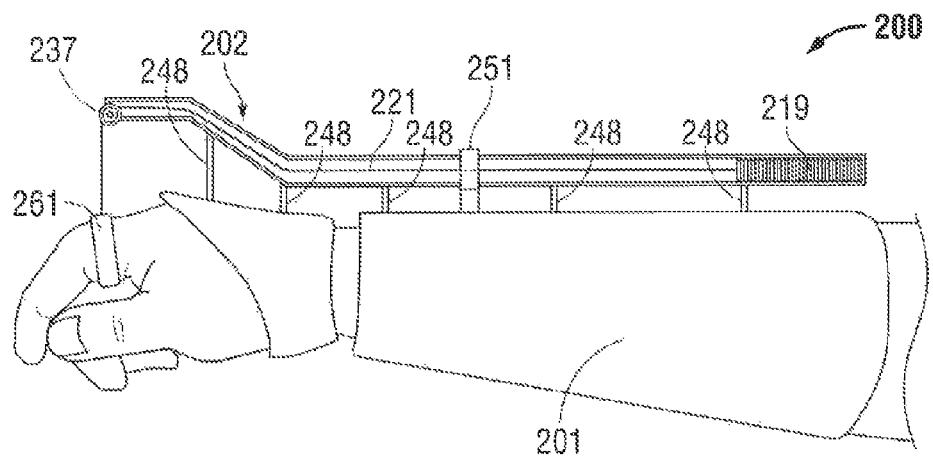
FIG. 3A is a side view of a dynamic traction apparatus according to an alternate embodiment of the present disclosure shown in use.
Figure 3B:
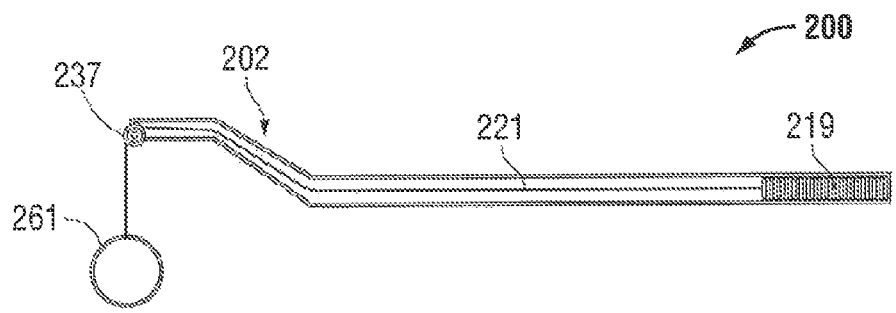
FIG. 3B is an side view of the dynamic traction apparatus depicted in FIG. 3A.
Figure 3C:
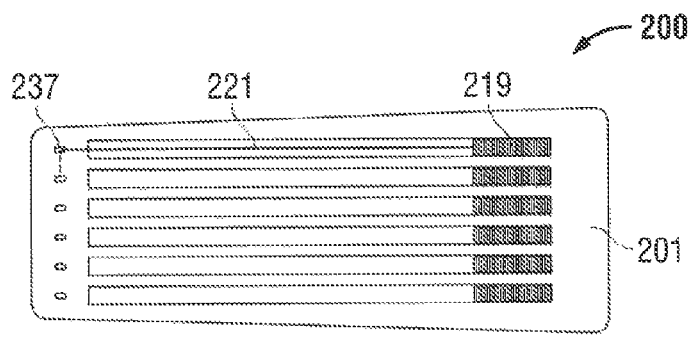
FIG. 3C is a top, elevational view of the dynamic traction apparatus of FIG. 3A with parts removed to illustrate a channel frame of the dynamic traction apparatus.

Channel frame 111 includes a pair of distal apertures 120a, 120b that are provided on corresponding lateral extensions 122a, 122b (see FIGS. 1A-1B). Distal apertures 120a, 120b align with corresponding proximal apertures 127a, 127b on bridge mount 125 for receiving therethrough corresponding female ends of support members 128 that are configured to engage corresponding male ends of set screws 130. Set screws 130 function similar to that of screws 112a, 112b. Unlike screws 112a, 112b, however, set screws 130 are configured to be hand tightened and loosened for coupling channel frame 111 to bridge mount 125. Other devices, e.g., pins, bolts, rivets, etc., may be utilized in place of set screws 130 and support members 128 for channel frame 111 to bridge mount 125.

Bridge mount portion 125 includes a generally elongated configuration having a medial portion with a generally hourglass configuration; this hourglass configuration is designed to accommodate wrists of various patients. In embodiments, bridge mount portion 125 may be relatively straight. Bridge mount portion 125 is removably coupleable to one or both of the mounting portion 101 and the channel frame 111. Although, bridge mount portion 125 may be permanently fixed to the channel frame 111 portion. As shown in the illustrated embodiment, bridge mount portion 125 is removably coupleable to the channel frame 111 via the aforementioned configuration of set screws 130 and support members 128. Distal apertures 127a, 127b include a generally arcuate configuration and are configured to allow bridge mount portion 125 to pivot or swivel with respect to channel frame 111 about the longitudinal axis "A-A". Specifically, prior to tightening set screws 130, a user may pivot bridge mount portion 125 to the right or left of channel frame 111. The amount of swivel in the left or right direction may vary for a particular apparatus 100. In the illustrated embodiment, bridge mount portion 125 is configured to swivel from about 10° to about 15° to the left or right of channel frame 111.

Bridge mount portion 125 includes one or more bridges 133 that are disposed at a distal end thereof. In the illustrated embodiment, one (1) bridge 133 is provided at a distal end of bridge mount portion 125 and extends transverse along a "B-B" axis that is orthogonal to the longitudinal axis "A-A" (see FIGS. 1A-1B). Bridge 133 is configured to guide coupling members 121 to one or more fingers of a patient. Bridge 133 may serve as a fulcrum, pulley, or otherwise to bend coupling members 121 at an angle relative to longitudinal axis "A-A" of apparatus 100 to lead coupling members 121 to the fingers of the patient. In embodiments, the angle that bridge 133 bends coupling members 121 may range from about 0° to about 130°. In an embodiment, the angle that bridge 133 bends coupling members 121 may range from about 5° to about 100°. In an embodiment, the angle that bridge 133 bends coupling members 121 may range from about 10° to about 90°. In embodiments, bridge 133 may be utilized to provide tension to coupling member 121 and/or to select a desired tension for a specific finger of a patient. Moreover, bridge 133 may be moveable to alter height or any position relative to the bridge mount portion 125.

Bridge 133 includes two generally upright extensions 132a, 132b of suitable configuration that are configured to operably support an axle 139 therethrough. Upright extensions 132a, 132b are identical to one another and include apertures (not explicitly shown) that are configured to receive opposing ends of axle 139 therethrough. Axle 139 may have any suitable configuration. In the illustrated embodiment, axle 139 is in the form of a solid rod or bar and is supported a predetermined distance above bridge mount portion 125.

One or more wheels 137 may be operably coupled to axle 139 and configured to rotate when the coupling members 121 translates (and/or stretches) distally. In the illustrated embodiment, eight (8) wheels are provided on axle 139 and are configured to rotate thereabout when a corresponding coupling member 121 is engaged therewith. Each wheel 137 defines a bridge channel 135 along an outer circumferential surface thereof. Bridge channels 135 are configured to receive a corresponding coupling member 121 therealong to maintain the coupling members 121 is a substantially straight configuration so as to prevent entanglement of the coupling members 121. As can be appreciated, more of fewer wheels 137 may be provided on axle 139. Wheels 137 provide a clinician with flexibility to optimize coupling members 121 location relative to fingers of a patient to accommodate different hand and/or finger sizes.

In embodiments, wheels 137 may be omitted and one or more bridge channels 135 may be defined through axle 129 and configured to function similarly to wheels 137. As can be appreciated, this may depend on the contemplated needs of a clinician, manufacturer's preference and/or specific therapy regiment.

An upright pin rod 141 is provided on bridge mount portion 125 and located distal of wheels 137. Pin rod 141 extends substantially parallel to axel 139 and may be utilized to guide coupling members 121 between wheels 137 and connection member 123.

Bridge mount portion 125 includes proximal apertures 129a, 129b that are defined through respective lateral extensions 138a, 138b. Apertures 129a, 129b are configured to receive one or more of the aforementioned straps therethrough to facilitate coupling apparatus 100 to a patient.

An optional removably coupleable cover 143 of suitable configuration may be provided with apparatus 100 and configured substantially enclose channel frame 111 when coupled thereto. Specifically, cover 143 may cover each of channels 113 (or a portion thereof) thereby protecting channels 113 from accumulating dirt, entanglement of coupling members 121 and/or damage to the resilient members 119. Cover 143 is removable to allow resilient members 119 and/or coupling members 121 to be accessed, changed, modified, fixed, etc. In the illustrated embodiment, a press or friction fit is utilized to couple cover 143 to channel frame 111. In embodiments, however, cover 143 may be permanently affixed to channel frame 111 to cover channels 113.

Moreover, a removable cover (not shown) of suitable configuration may be utilized to cover (or partially cover) bridge mounting portion 125 and/or component associated therewith. As can be appreciated, a press or friction fit may be utilized for coupling the removable cover to bridge mounting portion 125.

Operation of apparatus 100 is now described. For illustrative purposes, apparatus 100 is assumed in an assembled configuration and with cover 143 coupled thereto. Moreover, a cast that extends from a wrist of a patient to an elbow of the patient is presumed already affixed to a patient arm.

Apparatus 100 may, initially be coupled to an underside of a patients arm to the cast via the aforementioned strap configurations. If needed, proximal and distal support members 109a. 109b may be adjusted as described above to compensate with a gap between the cast and patient contact side 103 of mounting portion 101. Thereafter, finger caps 123 may be coupled to a finger of a patient. For illustrative purposes, the finger cap 123 is shown coupled to a middle finger of a patient.

Thereafter, a patient may extend or move the finger (or fingers) that are coupled to the finger caps 123, e.g., the middle finger, distally against the force provided by resilient members 119. This distal movement may be repeated based on a specific therapy regiment previously prescribed by a clinician.

The restorative force of the resilient members 119 provides muscle/ligament/tendon/bone/etc. therapy and facilitates in the healing of the injured limb. In accordance with the instant disclosure, apparatus 100 allows for a patient with an injured and affixed limb to safely and beneficially perform physical therapy. As can be appreciated, this advances recovery and prevents atrophy of the injured muscles, bones, ligaments, etc. Moreover, the aforementioned drawbacks that are, typically, associated with conventional apparatuses are reduced, if not, eliminated by the unique configuration of internal frame 111 and operable components associated therewith.

From the foregoing and with reference to the various figure drawings, those skilled in the art will appreciate that certain modifications can also be made to the present disclosure without departing from the scope of the same. For example, while apparatus 100 is configured for coupling to an underside of a patient's arm, certain modifications may be made to the apparatus 100 for coupling to different areas of a limb of a patient, e.g., a dorsal portion of a patient's arm.

Specifically, with respect to FIGS. 3A-3D a dynamic traction apparatus 200 according to an alternate embodiment of the instant disclosure is illustrated. Apparatus 200 is substantially similar to apparatus 100, accordingly only those aspects unique to apparatus 200 are described.

A tube structure 202 may be designed such that a coupling member 221 exits a distal opening 204 of the tube structure 202 and is connected to a finger of a patient at approximately a 90 degree angle to the tube 202. Dorsal embodiments may include base portion 201, i.e., dorsal splint or Exos splint, attached via legs 248 to tube structure 202. Legs 248 affix tube structure 202 to base portion 201 in a manner which suspends/supports tube structure 202 from base portion 201 creating space therebetween.

Tube structure 202 includes a resilient member 219, a coupling member 221 and a wheel 237, all of which function similar to their corresponding components described above. Each of resilient member 219 and coupling member 221 may be positioned or encased within tube structure 202 with coupling member 221 exiting a distal end of tube structure 202 and passing over wheel 237. A Guide 251 (e.g., a slip coupling) may be utilized to adjust tube structure 202 in order to slide tube proximally and/or distally (and/or side-to-side) to create a certain angle between the apparatus 200 and a finger of the patient. For example, tube structure 202 may be adjusted to create a 90 degree angle between apparatus 200 and a finger of a patient. The coupling member 221 may be connected to a finger as described above, such as a finger cap 123 and/or through a loop 261 of suitable configuration as shown. Other than an area of attachment to a persons arm, apparatus 200 operates substantially similar to that of apparatus 100.

Operation of apparatus 200 is now described. For illustrative purposes, apparatus 200 is assumed in an assembled configuration and a cast is presumed affixed to a patient arm. Apparatus 200 may, initially be coupled dorsally to a patients arm via the aforementioned strap configurations. Thereafter, loop 261 may be positioned on a finger of a patient. For illustrative purposes, loop 261 is shown coupled to an index finger of a patient.

Thereafter, a patient may extend or move the index finger in a manner as described above. This movement may be repeated based on a specific therapy regiment previously prescribed by a clinician. The restorative force of the resilient members 219 provides muscle/ligament/tendon/bone/etc. therapy and facilitates in the healing of the injured limb.

Aside from recovery after injury or surgery, the herein described apparatuses 100, 200 may also be used for various hand diagnoses, such as extensor tendon repair or nerve injuries/hand weakness, improve function or strength of an injured hand/finger.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A dynamic traction apparatus configured for removably coupling to an arm of a patient that is in traction, comprising:
   a mounting portion including a mounting portion configured to support a channel frame thereon, the channel frame including at least one channel defined therein and extending along a length thereof and at least one corresponding resilient member positioned adjacent the at least one channel;
   at least one resilient member operably coupleable to the frame;
   at least one coupling member including a proximal end coupled to the at least one resilient member; and
   a bridge mount removably coupleable to the channel frame and including a bridge extending transverse to a longitudinal axis defined through the mounting portion, the bridge including at least one wheel disposed in substantial alignment with the at least one channel of the channel frame such that a distal end of the coupling member is selectively coupleable to a finger of a patient.

2. The dynamic traction apparatus according to claim 1, wherein the channel frame includes a plurality of channels and a corresponding plurality of resilient members that are positioned adjacent thereto, and a corresponding plurality coupling members couple to a respective one of the resilient members, and wherein the bridge includes a plurality of wheels.

3. The dynamic traction apparatus according to claim 1, wherein the mounting portion includes a pair of proximal strapping apertures and a pair of distal strapping apertures that are configured to receive corresponding straps therethrough that are configured to couple the dynamic traction apparatus to an arm of a patient.

4. The dynamic traction apparatus according to claim 1, wherein the channel frame includes a pair of distal apertures a having a generally elongated configuration that are in alignment with a pair of corresponding proximal apertures on the bridge mount, the proximal apertures on the bridge mount including a generally arcuate configuration and configured to allow pivotable movement of the bridge mount with respect to the channel frame.

5. The dynamic traction apparatus according to claim 4, wherein coupling devices are configured for passage through the pair of distal apertures on the channel frame and proximal apertures on the bridge mount and are configured couple the channel frame and bridge mount one another and provide adjustment of the dynamic traction device with respect to an arm of a patient when the dynamic traction device is coupled thereto.

6. The dynamic traction apparatus according to claim 1, wherein the at least one resilient member is in the form of a coil spring.

7. The dynamic traction apparatus according to claim 1, wherein the at least one coupling member is selected from the group consisting of a wire, a string, a cable and a cord.

8. The dynamic traction apparatus according to claim 1, wherein the bridge includes a pair of opposing upright extensions that are configured to support an axle thereon, wherein the at least one wheel is rotatably disposed on the axle.

9. The dynamic traction apparatus according to claim 1, further including a cover portion that is removably coupleable to the channel frame and configured to substantially enclose the channel frame when coupled thereto and, wherein the mounting portion, mounting portion, channel frame, cover and bridge mount are formed from a relatively rigid plastic material.

* * * * *